(12) United States Patent
Santiago Fernandez et al.

(10) Patent No.: US 7,026,519 B2
(45) Date of Patent: Apr. 11, 2006

(54) OBTAINING TERT-BUTANOL

(75) Inventors: Silvia Santiago Fernandez, Oberhausen (DE); Andreas Beckmann, Recklinghausen (DE); Franz Nierlich, Marl (DE); Dieter Reusch, Marl (DE)

(73) Assignee: Oxeno Olefinchemie GmbH, Marl (DE)

( * ) Notice: Subject to any disclaimer, the term of this patent is extended or adjusted under 35 U.S.C. 154(b) by 44 days.

(21) Appl. No.: 10/893,306

(22) Filed: Jul. 19, 2004

(65) Prior Publication Data

US 2005/0043571 A1 Feb. 24, 2005

(30) Foreign Application Priority Data

Aug. 22, 2003 (DE) ................................. 103 38 581

(51) Int. Cl.
*C07C 29/04* (2006.01)
(52) U.S. Cl. ...................... 568/895; 568/896; 568/897; 568/898; 568/899; 568/900; 568/901
(58) Field of Classification Search ................ 568/895, 568/896, 897, 898, 899, 900, 901
See application file for complete search history.

(56) References Cited

U.S. PATENT DOCUMENTS

| 4,284,831 | A | 8/1981 | Okumura et al. |
| 4,307,257 | A | 12/1981 | Sada et al. |
| 4,327,231 | A | 4/1982 | Okumura et al. |
| 5,518,699 | A | 5/1996 | Kashnitz et al. |
| 6,111,148 | A | 8/2000 | Ogawa et al. |
| 2004/0171891 | A1 | 9/2004 | Scholz et al. |

FOREIGN PATENT DOCUMENTS

| DE | 25 38 036 | 3/1977 |
| DE | 30 25 262 | 2/1981 |
| DE | 30 31 702 | 3/1981 |
| DE | 102 59 413 | 12/2002 |
| DE | 102 60 991 | 7/2004 |
| DE | 103 30 710 | 7/2004 |
| EP | 0 010 993 | 5/1980 |
| EP | 1 431 264 | 6/2004 |
| GB | 2 060 616 | 5/1981 |

OTHER PUBLICATIONS

U.S. Appl. No. 10/790,706, filed Mar. 3, 2004, Beckmann et al.
U.S. Appl. No. 10/805,256, filed Mar. 22, 2004, Beckmann et al.
U.S. Appl. No. 10/790,707, filed Mar. 3, 2004, Beckmann et al.
U.S. Appl. No. 10/487,950, filed Mar. 5, 2004, Beckmann et al.
U.S. Appl. No. 10/893,306, filed Jul. 19, 2004, Fernandez et al.
U.S. Appl. No. 10/739,086, filed Dec. 19, 2003, Scholz et al.
U.S. Appl. No. 10/868,904, filed Jun. 17, 2004, Beckmann et al.

*Primary Examiner*—Elvis O. Price
(74) *Attorney, Agent, or Firm*—Oblon, Spivak, McClelland, Maier & Neustadt, P.C.

(57) ABSTRACT

The invention relates to a process for preparing tert-butanol (TBA) by reacting isobutene-containing hydrocarbon mixtures with water over acidic solid catalysts in a plurality of reactors, wherein the conversion is increased upstream of the last reactor by removing a portion of the TBA present in the reaction mixture.

9 Claims, 2 Drawing Sheets

OBTAINING TERT-BUTANOL

BACKGROUND OF THE INVENTION

1. Field of the Invention

Figure 1:
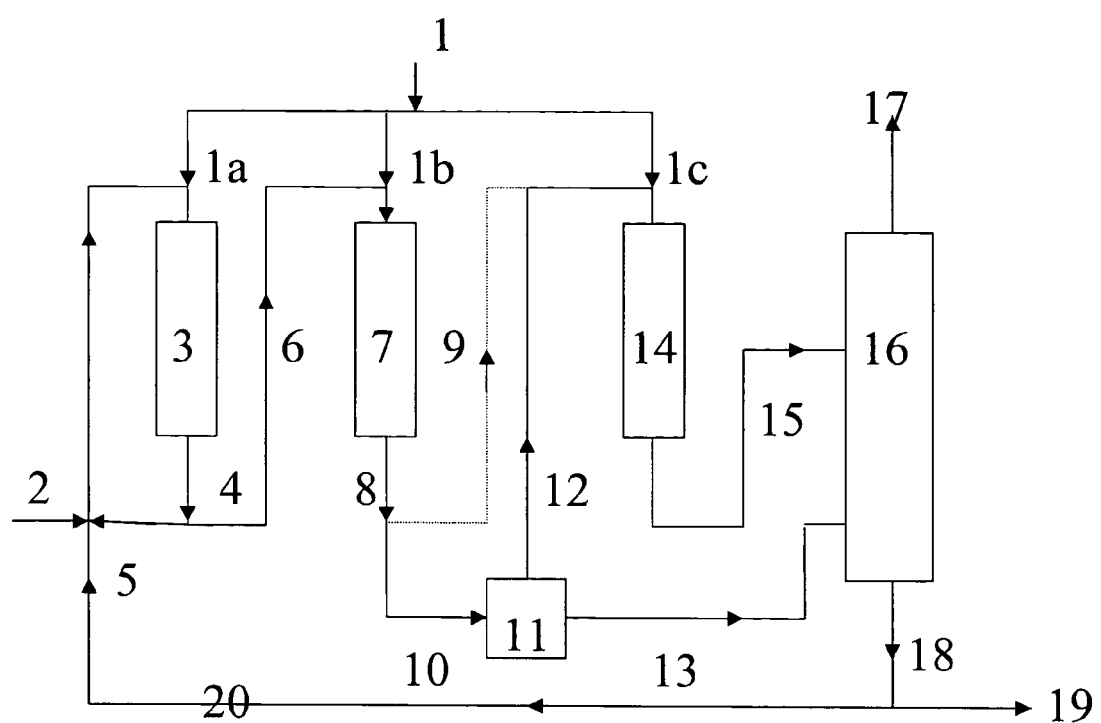

The invention relates to a process for preparing tert-butanol (TBA) by reacting isobutene-containing hydrocarbon mixtures with water over acidic solid catalysts in a plurality of reactors, wherein the conversion is increased upstream of the last reactor by removing a portion of the TBA present in the reaction mixture.

2. Description of the Background

Tert-butanol (TBA) is an important product prepared on the industrial scale and is used as a solvent and as an intermediate for the preparation of methyl methacrylate. It is a precursor for the preparation of peroxides such as peroxy ketals, peresters or dialkyl peroxides, having at least one tertiary butyl group. These compounds are used as oxidizing agents and as initiators for free-radical reactions, for example olefin polymerization or crosslinking of plastics. Tert-butanol is used as an intermediate for obtaining pure isobutene from isobutene mixtures. In addition, it is a reagent for introducing tertiary butyl groups. Its alkali metal salts are strong bases which find use in many syntheses.

Tertiary butanol can be obtained by acid-catalyzed addition of water to isobutene. Technical-grade isobutene mixtures frequently also contain other olefins, for example 2-butenes. Industrial processes therefore employ conditions in which almost exclusively the isobutene but not the other olefins is hydrated, and side reactions such as homo- or heterooligomerization of the olefins are virtually fully suppressed. Such processes commonly operate in the liquid phase and can be divided into two groups: a) processes in which the conversion is effected in an aqueous catalyst solution and b) heterogeneous catalytic processes in which solid catalysts which are insoluble in the reaction phase are used.

The hydration of isobutene to tert-butanol with the aid of solid acidic catalysts which are soluble neither in the reactants nor in the products has the advantage that the reaction mixture is acid-free and can be worked up to tert-butanol without losses by dissociation or by other side reactions. The reaction proceeds on the surface of the catalyst. So that a reaction occurs, both reaction partners have to be at the active site of the catalyst at the same time. This is complicated by water and isobutene or an isobutene-containing hydrocarbon mixture not being mutually miscible. In order to obtain acceptable conversions, solvents are used which enable a homogeneous mixture of water and isobutene starting mixture.

DE 30 31 702 A1 describes methanol for this purpose as a solvent both for water and for isobutene or for an isobutene-containing hydrocarbon mixture. The products obtained are both tert-butanol and methyl tert-butyl ether.

In EP 0 010 993 A1, aliphatic carboxylic acids having from 1 to 6 carbon atoms are used as the solvent for both reactants. The by-products formed are the tertiary butyl esters of these acids. These have to be hydrolyzed to tert-butanol and carboxylic acids.

In DE 30 31 702 A1, sulfolanes are used, and, in U.S. Pat. No. 4,327,231, neo-type polyhydric alcohols, for example neopentyl glycol. These solvents have to be removed from the tert-butanol. In addition, there is the risk that the solvent used is destroyed in the long-term operation of such a plant.

In order to avoid these disadvantages, the target product, TBA, is used as solubilizer in some processes. Such processes are described, for example, in WO 99/337755 or DE 30 25 262. In these processes, a mixture of a hydrocarbon fraction which comprises isobutene, TBA and water is converted in a reactor battery over acidic catalysts arranged in a fixed bed. The first reactor is usually operated in loop mode and the other in straight pass. Upstream of each further reactor, water of reaction may be metered in. The effluent of the last reactor is separated by distillation into a hydrocarbon mixture comprising the unconverted isobutene and crude TBA. A portion of the crude TBA is recycled into the first reactor. The other portion may be used as such or worked up to TBA and/or TBA/water azeotrope.

In these processes, the TBA content increases and the isobutene content decreases from reactor to reactor as a consequence of the progress of the reaction. The composition of the reaction mixture approaches, at a decreasing rate, the thermodynamic equilibrium between water, isobutene and TBA, so that complete conversion cannot be achieved. Starting from technical-grade isobutene streams, for example raffinate I, conversions of only approx. 82% are achieved.

In the application DE 102 60 991 which was yet to be published at the priority date of the present application, a process is described for preparing TBA in which a relatively complicated reactive distillation is used.

SUMMARY OF THE INVENTION

In view of this background, it is an object of the present invention to improve the economic viability of the process for TBA preparation.

It has now been found that, surprisingly, the conversions of isobutene to TBA can be increased and thus also the economic viability improved when the process is carried out in at least two reactors connected in series, by removing a portion of the TBA from the reaction effluent of the penultimate reactor, before feeding it into the last reactor.

The present invention therefore provides a process for preparing tert-butanol (TBA) by converting a mixture which comprises water, TBA and an isobutene-containing hydrocarbon mixture over an acidic catalyst in a reactor battery which has at least two reactors at from 30 to 120° C., and subsequently removing the unconverted hydrocarbons by distillation, which comprises removing a portion of the TBA from the reactor effluent of at least one reactor which is not the last reactor of the reactor battery before the remainder of the TBA-depleted reactor effluent is passed into the subsequent reactor.

DETAILED DESCRIPTION OF THE DRAWINGS

FIG. 1: a flow diagram for an embodiment of the process of the present invention.

Figure 2:
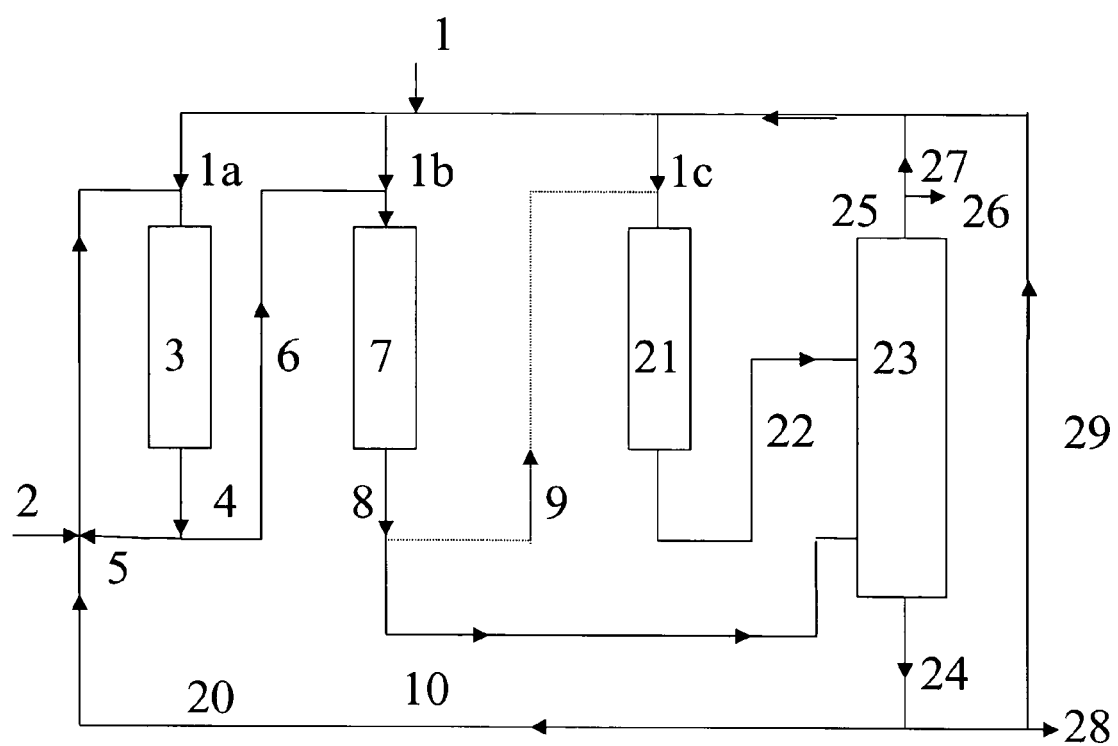

FIG. 2: a flow diagram for another embodiment of the process of the present invention.

DETAILED DESCRIPTION OF THE INVENTION

In industrial processes for preparing TBA, the concentration of an isobutene in the reaction mixture decreases and the concentration of TBA increases from reactor to reactor as a consequence of the progress of the reaction. At a decreasing rate from reactor to reactor, the composition of the reaction mixture approaches the thermodynamic equilibrium between isobutene, water and TBA. In order increase the reaction rate and thus the space-time yield and to achieve a higher conversion of isobutene, the concentration of isobutene is increased and the concentration of TBA reduced in the process according to the invention. This is effected by removing a portion of the TBA from the reaction effluent of a reactor and passing the reduced-TBA reaction mixture into the next reactor, preferably the last. The process according to the invention has the advantage that distinctly higher conversions are attained in comparison to conventional processes. The higher conversions additionally make the process more economically viable. A very particular advantage may be achieved when the reaction effluent is depleted in TBA by fully or partly conducting it into the crude TBA column and using it for depletion of TBA by conducting a portion of the top product of the crude TBA column as a TBA-depleted product stream and optionally conducting a portion of the bottoms of the column into the subsequent reactor. In this procedure, it is possible to dispense with an additional column for depleting the reactor effluent of the reactor which is not the last of the reactor battery in TBA. In this way, the capital costs can be reduced and thus the economic viability increased.

The process according to the invention is described hereinbelow without the invention being restricted to these embodiments. When ranges and preferred ranges are specified in the text which follows, theoretically possible subranges which lie within these ranges are also included in the disclosure content of the present invention, without these being explicitly specified for reasons of better clarity.

In the process according to the invention for preparing TBA by converting a mixture which comprises water, TBA and an isobutene-containing hydrocarbon mixture over an acidic catalyst in a reactor battery which has at least two reactors at from 30 to 120° C., and subsequently removing the unconverted hydrocarbons by distillation, a portion of the TBA is removed from the reactor effluent of at least one reactor, preferably of the penultimate reactor, which is not the last of the reactor battery, before the TBA-depleted reactor effluent is passed into the subsequent reactor, preferably the last reactor.

Preference is given to effecting the removal of a portion of the TBA from the reaction effluent of the reactor which is not the last of the reactor battery by distillation or rectification, by conducting the TBA-depleted product stream into the subsequent reactor and feeding the TBA-enriched product stream together with the effluent of the subsequent reactor into a column for working up crude TBA (crude TBA column). The removal of a portion of the TBA may be effected by flash evaporation/simple evaporation or simple distillation.

In the process according to the invention, the TBA removal between two reactors is effected especially when the reactor effluent between the two reactors has an isobutene concentration of less than 15% by mass, in particular less than 12% by mass, or a TBA concentration of greater than 40% by mass, in particular greater than 45% by mass. Typically, these values correlate with each other. However, this is not necessarily a requirement. Particular preference is given to effecting the removal of the TBA from a reactor effluent of at least one reactor (which is not the last of the reactor battery) which has a content of isobutene of less than 15% by mass. The TBA removal brings the TBA concentration in the feed of the next reactor, preferably of the last reactor, to values of from 10 to 50% by mass, in particular from 20 to 45% by mass and more preferably from 25 to 40% by mass. The removal of the TBA is thus preferably effected in such a way that the TBA-depleted product which is conducted into the subsequent or last reactor has a content of TBA of from 10 to 50% by mass, in particular from 20 to 45% by mass and more preferably from 25 to 40% by mass.

The TBA removal in the process according to the invention, is preferably effected by distillation. There are several possible embodiments. Two embodiments of the process according to the invention are illustrated by way of example in FIG. 1 and FIG. 2. In the first preferred embodiment (FIG. 1), the entire effluent of a reactor, preferably the penultimate reactor, or a portion thereof, is separated into a TBA-depleted top product which preferably contains the low-boiling hydrocarbons together with the unconverted isobutene and also water and TBA, and into a TBA-enriched bottom product which preferably comprises substantially TBA, small amounts of C4 hydrocarbons, water and high-boiling by-products. The top product is introduced into the next reactor, preferably the last reactor, together with additional water and optionally with undistilled reactor effluent. The bottom product may be fed into a separating column (for example apparatus 16 in FIG. 1) or fed to another work-up.

Since the top product which is fed into the next reactor should likewise contain TBA as a solubilizer for water, a number of vertical plates of from 0.3 to 1 is sufficient in the distillation. The distillative separation may therefore appropriately be carried out as a flash evaporation/simple evaporation. In this way, it is possible to achieve, for example, a reduction in the TBA content in the top product from a stream having virtually 50% by mass of TBA to values of approx. 35% by mass.

The evaporation is effected either at the pressure of the penultimate reactor, i.e. in the range from 7 to 14 barabs. or at a reduced pressure in the range from 4 to 8 barabs. The selection of the pressure depends substantially upon the means of heat recovery in the plant. The evaporators used can be customary apparatuses such as forced-circulation or natural-circulation evaporators, or any other vertical or horizontal vessels having heating apparatus. The top product usually leaves the evaporator in vapor form and has to be subsequently condensed and is then passed into the reactor or else condensed in the reactor inlet, so that the reaction can proceed in the liquid phase.

In the second embodiment (FIG. 2) of the process according to the invention, the reaction effluent of a reactor which is not the last of the reactor battery, preferably of the penultimate reactor, is fully or partly passed, together with the reaction effluent of the last reactor, into a column, in particular a column for removing crude TBA (crude TBA column, apparatus 23 in FIG. 2). A portion of the TBA-depleted top product of this column which comprises hydrocarbons together with the unconverted isobutene and a portion of the TBA-enriched bottom product of this column (crude TBA) is fed into a subsequent reactor, preferably the last reactor, with the addition of water of reaction and optionally of a substream of a reactor effluent.

The two embodiments of the process according to the invention are shown by way of example as block schemes in FIG. 1 and FIG. 2 to illustrate the invention. These schemes each have three reactors. It will be appreciated that the process according to the invention for preparing TBA may also be carried out using two, three or more than three reactors.

In the first embodiment of the process according to the invention in FIG. 1, process water (1*a*), isobutene-containing hydrocarbon feed mixture (2), crude TBA (20) and a portion (5) of the reaction effluent (4) from the reactor (3) are introduced into the reactor (3). A portion (6) of the reaction effluent (4) is converted in the second reactor (7)

together with process water (1b). The entire effluent (8) from reactor (7) or a portion (10) thereof is separated in the distillation or evaporator unit (11) into a low-isobutene or virtually isobutene-free bottom product (13) and into an isobutene-rich top product (12). The bottom product (13) is conducted into the distillation column (16). The top product (12) is fed into the third reactor (14) together with process water (1c) and optionally with undistilled effluent (9). The effluent (15) of the reactor (14) is separated together with stream (13) in the column (16) into a top product (17) which comprises isobutene and other low-boiling hydrocarbons, and into crude TBA (18). A portion (20) of the crude TBA is recycled into the reactor (3). The other portion (19) may be worked up into pure TBA and/or TBA/water azeotrope in a plant which is not shown.

One possible connection of apparatus and streams in accordance with the second embodiment of the process according to the invention is shown by FIG. 2. Process water (1a), isobutene-containing hydrocarbon feed mixture (2), crude TBA (20) and a portion (5) of the effluent (4) from the reactor (3) are passed into the reactor (3). A portion (6) of the effluent (4) is converted together with process water (1b) in the second reactor (7). The effluent (8) of the reactor (7) is fully or partly (10) passed into the distillation column (23). It is separated there into a top product (25) which comprises low-boiling hydrocarbons together with the isobutene which has not been fully converted, and crude TBA (24). A portion (27) of the top product (25) is optionally passed into the third reactor (21) together with a portion (29) of the crude TBA (24) and process water (1c), and optionally with a portion (9) of the effluent (8) from the second reactor (7). The effluent (22) of the third reactor (21) is fed into the distillation column (23). The second portion (20) of the crude TBA (24) is recycled into the first reactor (3). The third portion (28) of the crude TBA may be worked up to pure TBA and/or TBA/water azeotrope in a plant which is not shown. The hydrocarbon stream (26) is discharged from the process.

The starting material used in the process according to the invention may be an isobutene-containing hydrocarbon mixture, or optionally also pure isobutene. The isobutene-containing hydrocarbon mixture preferably contains no acetylene derivatives, less than 5 000 ppm of dienes and no further olefins having one or two branch(es) on the olefinic double bond.

Technical-grade mixtures which comprise isobutene are, for example, light petroleum fractions from refineries, C4 fractions from FCC units or steam crackers, mixtures from Fischer-Tropsch syntheses, mixtures from dehydrogenation of butanes, mixtures from skeletal isomerization of linear butenes, mixtures resulting by metathesis of olefins or other industrial processes.

These mixtures, optionally after removal of the polyunsaturated compounds, are used in the process according to the invention. For example, a suitable isobutene mixture may be obtained from the C4 fraction of a steam cracker by extracting the butadiene or by selectively hydrogenating it to linear butenes. This feedstock (raffinate I or selectively hydrogenated crack C4) consists of n-butane, isobutane, the three linear butenes and isobutene, and is a preferred reactant for the process according to the invention. The isobutene content in the raffinate I used with preference is typically in the range from 30 to 60%.

Optionally, raffinate I, hydrogenated crack C4 or a hydrocarbon mixture having a similar composition may be hydroisomerized in a reactive column. In this way, a mixture of isobutene (and in some cases 1-butene) and isobutane may be obtained, which may then be used as a raw material in the inventive TBA synthesis (stream (2)).

The concentration of isobutene in the hydrocarbon mixture may vary within a wide range. However, owing to the economic viability of the process, preference is given to using hydrocarbon mixtures having an isobutene concentration of greater than 30% by mass, preferably greater than 40% by mass.

The catalyst used is preferably an acidic ion exchanger which is soluble neither in the feedstock mixture nor in the product mixture. The catalyst must not supply acidic substances to the product mixture under the reaction conditions either by hydrolysis or by other reactions, because this would lead to yield losses in the workup of the reaction mixture.

The activity of the suitable catalysts has to be such that they bring about the hydration of isobutene under the reaction conditions, but barely that of unbranched olefins. In addition, they must barely catalyze the oligomerization of olefins.

A suitable group of catalysts is solid ion exchange resins having sulfonic acid groups. Particularly suitable ion exchange resins are, for example, those which are prepared by sulfonating phenol/aldehyde condensates or cooligomers of aromatic vinyl compounds. Examples of aromatic vinyl compounds for preparing the cooligomers are: styrene, vinyltoluene, vinylnaphthalene, vinylethylbenzene, methylstyrene, vinylchlorobenzene, vinylxylene and divinylbenzene. In particular, the cooligomers which result by reaction of styrene with divinylbenzene are used as a precursor for the preparation of ion exchange resins having sulfone groups. The resins may be in gel form, macroporous form or honeycomb form. Some trade names under which suitable resins of the styrene-divinylbenzene type are sold include: Duolite C20, Duolite C26, Amberlyst 15, Amberlyst 35, Amberlite IR-120, Amberlite 200, Dowex 50, Lewatit SPC 118, Lewatit SPC 108, K2611, OC 1501.

The properties of these resins, in particular specific surface area, porosity, stability, swelling or shrinkage and exchange capacity, may be varied by the preparation process.

In the process according to the invention, the ion exchange resins are preferably used in their H form. The ion exchange capacity is between 2 and 7 eq/kg, in particular 3 and 6 eq/kg (based on moist commercial resin). Preference is given to using macroporous resins, for example Amberlyst 15, Amberlyst 35, Lewatit SCP 118, Lewatit SCP 108 or K2631. The average particle size of the resin may preferably be from 0.5 to 2 mm. The particle size distribution selected may be narrow or wide. Preference is given to using ion exchange resins having very uniform particle size (monodisperse resins). When a plurality of reactors is used, they may be filled with resin of the same or different particle sizes (and particle size distribution).

Optionally, the ion exchange resins may be used not only as spheres, but also as shaped bodies, for example cylinders, rings or spheres, or polymerized onto shaped bodies.

It may be advantageous, in reactors which are flowed through at high linear rates, to reduce the differential pressure, to use an ion exchange resin having a relatively large particle size, and, in reactors which are flowed through at a low linear rate, to achieve the optimum conversion, to use an ion exchange resin having a relatively small particle size.

In order to prevent the resin from releasing acidic groups during operation which might thus cause disruption in the workup section of the process, and in order to retain a high activity of the catalyst over a long period, the ion exchange resin may be pretreated, for example, by flushing with water, TBA or TBA/water mixtures, preferably in the temperature range from 40 to 120° C.

Since water is consumed by the hydration of isobutene, the water content in the reaction mixture falls constantly. In order to obtain a very high yield and reaction rate, it is advantageous to meter in further water. This could be done, for example, by feeding water at different points in a tubular reactor. However, it is difficult in practice to introduce precisely the required amount of water and to achieve a homogeneous solution immediately. It is technically more simple and therefore advantageous to connect a plurality of reactors in series and to feed in the required amount of water in each case before the entry of the reaction mixture into the reactor, i.e., for example, between the reactors.

The amount of water in the reactant mixture stems from a tert-butanol/water solution which, from the startup phase, is obtained in the process itself after the hydrocarbons have been removed, i.e. by recycling a portion of the reactor effluent. When this amount of water is not sufficient, water (water of reaction or a mixture with tert-butanol) is additionally fed in. The amount of water in the mixture which is fed to a reactor is dependent on the ratio of TBA to the C4 hydrocarbon mixture. Preference is given to using a maximum of as much water as is soluble in the TBA/C4 hydrocarbon mixture, so that the solution is homogeneous. In particular, apart from the last reactor in some cases, water contents are set in the TBA/C4 hydrocarbon mixture which are lower than the particular maximum solubilities. Very particularly, water concentrations are set as claimed in the DE 10259413.9 or DE 10330710.9, both incorporated herein by reference. Pure water or else a mixture with tert-butanol may be introduced into the further reactors. A portion of the TBA obtained by the reaction may also be recycled to prepare a homogeneous mixture with water and the isobutene-containing hydrocarbon mixture.

The process may be carried out in batchwise or continuous reactors which are typically used in the case of liquid/solid contact reactions. When continuous flow reactors are used, it is preferable, but not obligatory, to use a fixed bed. Where a fixed bed flow reactor is used, the liquid may flow upward or downward. Usually, preference is given to downward flow of the liquid.

It is also possible to operate the reactor with product recycling or in straight pass.

When tubular reactors are used, the ratio of length to diameter of the catalyst bed may be varied, either by the geometric dimensions of the reactor or by its fill level. At the same amount of catalyst and LHSV, different superficial velocities may thus be achieved. Reactors in which a portion of the reaction mixture is recycled may be operated, for example, at superficial velocities of from 12 to 60 m/h, very particularly of from 12 to 30 m/h. In the reactors which are flowed through in straight pass, the superficial velocities may be in the range from 0.8 to 55 m/h and particularly in the range from 1 to 25 m/h.

The LHSV in the case of reactors which are operated with product recycling is preferably from 0.3 to 10 h-1, in particular from 1 to 6 h-1. In the case of reactors which are operated in straight pass, the LHSVs are preferably in the range from 0.1 to 5.0 h-1, in particular in the range from 0.4 to 3 h-1.

The process according to the invention is carried out in at least two reactors connected in series which may each have the same or different reactor temperatures. Preference is given to carrying out the process in a plurality of reactors connected in series which have temperatures falling in the flow direction.

When one or more of the reactors are operated with product recycling, preference is given to setting a circulation factor (ratio of amount circulated to fresh feed) of from 0.1 to 10. The circulation factor for the first reactor is preferably from 1 to 5, in particular from 2 to 3.5.

In a preferred embodiment of the process according to the invention, the first reactor can be operated with product recycling and the further reactors in straight pass. The number of reactors used is preferably between 2 and 10, more preferably between 2 and 4.

Each reactor may be operated adiabatically or quasi-isothermally, i.e. with a temperature differential from reactor feed to reactor outlet of less than 10 K, preferably of less than 5 K and more preferably of less than 1 K. Too high a temperature rise is to be avoided owing to the unfavorable influence on equilibrium (dissociation) and the increase of side reactions.

The temperatures at which the process according to the invention is carried out are preferably from 30 to 120° C. At lower temperatures, the reaction rate is too low, and, at higher temperatures, side reactions, for example the oligomerization of the olefins, occur to an increased extent. Preference is given to operating the reactors in the temperature range from 35 to 80° C. The temperatures in different reactors may be the same or different within the range specified. In one process variant, the temperature falls from reactor to reactor in flow direction. Since the equilibrium position becomes more favorable with falling temperature, a higher conversion may thus be achieved. However, it is not viable to reduce the temperature below 35° C., because the reaction then becomes too slow for an industrial process.

For example, in the case of four reactors connected in series, the first may be operated at an average temperature of from 50 to 70° C., preferably from 60 to 70° C., the second at a temperature of from 50 to 60° C., the third at a temperature of from 40 to 50° C., preferably from 40 to 46° C., and the fourth reactor at a temperature of from 38 to 50° C., preferably from 38 to 42° C.

The inventive conversion may be carried out at a pressure equal to or above the vapor pressure of the hydrocarbon feed mixture at the particular reaction temperature, preferably at a pressure below 40 bar. In order to avoid evaporation problems in the reactors, the pressure should be from 2 to 4 bar higher than the vapor pressure of the reaction mixture.

The examples which follow are intended to illustrate the invention without restricting its field of application which is evident from the description and the claims.

EXAMPLES

The raffinate stream used for the experiments 1 to 3 had the following composition:

| | |
|---|---|
| n-butane: | 8.2 parts by mass |
| isobutane: | 2.3 parts by mass |
| 1-butene: | 29.8 parts by mass |
| 2-butene (cis + trans): | 14.3 parts by mass |
| isobutene: | 45.4 parts by mass |

This raffinate stream was converted in a laboratory experimental plant using water and recycled TBA as a solubilizer 4 reactors were connected in series, and the first reactor was operated as a circulation reactor. Reactors 1 to 3 consisted of fixed catalyst beds each having a catalyst volume of from 250 to 450 ml; the fourth reactor was operated at catalyst volume of 950 ml. The catalyst used was Amberlyst 35 or Amberlyst 15 in $H^+$ form. The product streams were analyzed by gas chromatography. The components n-butane, isobutane, 1-butene, 2-butene (cis+trans) were listed in total as a residual $C_4$. The compositions specified are based on product effluents in quasi-steady-state equilibrium which had been attained after an experimental time of from 20 to 30 hours. The pressure in the plant was 12 bar absolute; the laboratory column had a diameter of 50 mm and was operated at 6 bar absolute. The first reactor was operated at an inlet temperature of 55° C.; all further 3 reactors were operated at 50° C. For better comparability of the individual experiments, stream (20) was constantly supplemented with such an amount of additional water that a water content of 10.4 parts by mass was set in the mixture. This corresponds to an increased addition of process water at the first reactor.

Example 1 (Inventive)

The stream numbers in the following Table 1 correspond to those in FIG. 1. For the evaporation step (11), a heated laboratory pressure vessel was used. The feed of raffinate stream (raffinate I) was 0.3 kg/h.

TABLE 1

| Stream number | Stream designation (mass flow rate) | Parts by mass |
|---|---|---|
| 1 | process water (0.048 kg/h) | 91.3 water 8.7 TBA |
| 9 | bypass (0 kg/h) | |
| 10 | pre-flash (0.415 kg/h) | 6.8 isobutene 3.9 water 49.7 TBA 39.5 residual $C_4$ |
| 12 | flash raffinate (0.284 kg/h) | 8.9 isobutene 3.4 water 35.1 TBA 52.6 residual $C_4$ |
| 13 | flash TBA (0.131 kg/h) | 2.3 isobutene 5.2 water 81.4 TBA 11.1 residual $C_4$ |
| 15 | final reactor outlet (0.284 kg/h) | 5.2 isobutene 2.2 water 40.0 TBA 52.6 residual $C_4$ |
| 20 | residual TBA (0.066 kg/h) | 10.4 water 89.4 TBA |

The overall conversion achieved was: 87.0%

Example 2 (Comparative)

The stream numbers in the following Table 2 correspond to those in FIG. 1. Parts by mass are reported. The feed of raffinate stream (raffinate I) was 0.3 kg/h. Operation was effected without additional evaporation in order to investigate the effect on the conversion.

TABLE 2

| Stream number | Stream designation (mass flow rate) | Parts by mass |
|---|---|---|
| 1 | process water (0.052 kg/h) | 91.3 water 8.7 TBA |
| 9 | bypass (0 kg/h) | |
| 10 | pre-flash (0.415 kg/h) | 6.8 isobutene 3.9 water 49.7 TBA 39.5 residual $C_4$ |
| 12 | flash raffinate (0.415 kg/h) | see stream No. 10, no flash |
| 13 | flash TBA (0 kg/h) | No flash |
| 20 | residual TBA (0.066 kg/h) | 10.4 water 89.4 TBA |
| 15 | final reactor outlet (0.419 kg/h) | 5.7 isobutene 4.4 water 50.7 TBA 39.1 residual $C_4$ |

The overall conversion achieved was: 82.4%

Example 3 (Inventive)

The stream numbers in the following Table 3 correspond to those in FIG. 2. In each case, parts by mass are reported. The feed of raffinate stream (raffinate I) was 0.3 kg/h.

TABLE 3

| Stream number | Stream designation (mass flow rate) | Parts by mass |
|---|---|---|
| 1 | process water (0.051 kg/h) | 91.3 water 8.7 TBA |
| 9 | bypass (0 kg/h) | |
| 10 | penultimate reactor (0.415 kg/h) | 6.8 isobutene 3.9 water 49.7 TBA 39.5 residual $C_4$ |
| 27 | recycled distillate raffinate (0.280 kg/h) | 10.7 isobutene 0.9 water 0.8 TBA 87.7 residual $C_4$ |
| 29 | residual TBA (0.164 kg/h) | 6.2 water 93.8 TBA |
| 20 | recycled TBA (0.066 kg/h) | 10.4 water 89.4 TBA |
| 22 | final reactor outlet (0.447 kg/h) | 4.8 isobutene 2.7 water 37.5 TBA 55.0 residual $C_4$ |

The overall conversion achieved was: 85.4%

Comparison of the Examples:

Both the simple evaporation in Example 1 (according to the invention) and the novel connection of Example 3 (according to the invention) allowed the conversion to be distinctly increased in comparison to the conventional series connection of the reactors of Example 2 (comparative example).

This application is based on German application No. 103 38 581.9, filed on Aug. 22, 2003, and incorporated herein by reference in its entirety.

What is claimed is:

1. A process for preparing tert-butanol (TBA), comprising:
    converting a mixture which comprises water, TBA and an isobutene-containing hydrocarbon mixture over an acidic catalyst in a reactor battery which has at least two reactors at from 30 to 120° C., removing a portion of the TBA from the reactor effluent of at least one reactor which is not the last reactor of the reactor battery before the TBA-depleted reactor effluent is passed into the subsequent reactor, and removing the unconverted hydrocarbons by distillation.

2. The process of claim 1, wherein the removal of a portion of the TBA from the reaction effluent of the reactor which is not the last of the reactor battery is effected by distillation or rectification, and the process comprises conducting the TBA-depleted product stream into the subsequent reactor and feeding a TBA-enriched product stream together with the effluent of the subsequent reactor into a column for working up crude TBA.

3. The process of claim 1, wherein the removal of a portion of the TBA is effected by flash evaporation/simple evaporation or simple distillation.

4. The process of claim 1, wherein the reactor effluent from the reactor which is not the last of the reactor battery is fed fully or partly, together with the effluent of the last reactor, into a column for removing crude TBA (crude TBA column) and a portion of the top product and a portion of the bottom product of the crude TBA column are introduced into the last reactor.

5. The process of claim 1, wherein the removal of TBA is effected in such a way that the TBA-depleted product which is conducted into the subsequent or last reactor has a content of TBA of from 10 to 50% by mass.

6. The process of claim 1, wherein the removal of TBA is effected from a reactor effluent of at least one reactor which is not the last of the reactor battery and has a content of isobutene of less than 15% by mass.

7. The process of claim 1, wherein the reactor battery has two reactors.

8. The process of claim 1, wherein the reactor battery has three reactors.

9. The process of claim 1, wherein the reactor battery has three or more reactors.

* * * * *